United States Patent [19]

Brill

[11] Patent Number: 4,480,113

[45] Date of Patent: Oct. 30, 1984

[54] EPOXIDATION CATALYST AND PROCESS

[75] Inventor: William F. Brill, Skillman, N.J.

[73] Assignee: The Halcon SD Group, Inc., New York, N.Y.

[21] Appl. No.: 425,787

[22] Filed: Sep. 28, 1982

[51] Int. Cl.$^3$ .......................................... C07D 301/12
[52] U.S. Cl. ..................................................... 549/531
[58] Field of Search ........................................ 549/531

[56] References Cited

U.S. PATENT DOCUMENTS

| | | |
|---|---|---|
| 2,786,854 | 3/1957 | Smith et al. |
| 2,833,787 | 5/1958 | Carlson et al. |
| 3,351,635 | 11/1967 | Kollar. |
| 3,778,451 | 12/1973 | Poite. |
| 3,806,467 | 4/1974 | Watanabe et al. |
| 3,953,362 | 4/1976 | Lines et al. |
| 3,993,673 | 11/1976 | McMullen. |
| 4,026,908 | 5/1977 | Pralus et al. |
| 4,242,285 | 12/1980 | Renga ................. 549/531 |
| 4,286,068 | 8/1981 | Mares et al. ......... 549/531 |

FOREIGN PATENT DOCUMENTS 860776 11/1977 Belgium.
837464 6/1960 United Kingdom.

OTHER PUBLICATIONS

Milas, JACS, vol. 59, pp. 2342–2344, (1937).
Mugden and Young, J. Chem. Soc., pp. 2988–3000, (1949).
Bull Chem. Soc. Jap., 42, No. 6, pp. 1604–1608, (1969).
N. K. Mathur and R. E. Williams, J. Macromol. Sci.—Rev. Macromol. Chem., 15, (1), pp. 117–142, (1976).
R. Michels et al., in Makromol Chem., vol. 177, pp. 2311–2320, (1976).
Jacobson et al., JACS, 101:23, pp. 6946–6950, Nov. 7, 1979.

*Primary Examiner*—Norma S. Milestone
*Attorney, Agent, or Firm*—William C. Long; Riggs T. Stewart; Harold N. Wells

[57] ABSTRACT

The present invention relates to a novel tellurium catalyst and its preparation, and to a process for preparing oxirane compounds using the novel catalyst. Specifically, the invention relates to a novel catalyst in which tellurium is chemically bound to a solid aromatic-type resin and to the reaction of olefinic compounds with hydrogen peroxide in the presence of the bound tellurium catalyst to produce oxirane compounds.

2 Claims, No Drawings

EPOXIDATION CATALYST AND PROCESS

PRIOR ART

Methods are known in the art for the production of oxirane compounds. Ethylene oxide, for example, is prepared by the vapor phase molecular oxygen oxidation of ethylene over a supported silver catalyst. This procedure has not, however, proved applicable to other olefins.

Propylene oxide has been prepared from propylene by the chlorohydrin process but this procedure is no longer favored because of its high costs and problems of byproduct recycle or disposal. The chlorohydrin process has been largely superceded by the hydroperoxide process, see U.S. Pat. No. 3,351,635, which has achieved worldwide acceptance and which involves reaction of an organic hydroperoxide with an olefinic compound in the presence of certain catalysts. In this process, a co-product is generally produced which is derived from the hydroperoxide, e.g., tertiary butyl alcohol where tertiary butyl hydroperoxide is a reactant or styrene via alpha phenyl ethanol where ethyl benzene hydroperoxide is a reactant. Although the hydroperoxide process has achieved outstanding success, there are many cases where a process for production of oxirane compounds without production of a significant co-product are desirable.

Other processes for production of oxirane compounds include the peracid reactions, e.g., peracetic or perpropionic acid reaction with olefinic materials, but these processes are hazardous and expensive.

Methods have long been sought for the preparation of oxirane compounds by reaction of olefinic compounds with hydrogen peroxide. However, generally speaking such prior attempts have not been satisfactory—usually high amounts of diol are formed.

Milas, JACS, Vo. 59, p. 2342–2344 (1937) shows the hydroxylation of unsaturated compounds by reaction with hydrogen peroxide in the presence of Os, Ti, Zr, Th, V, Nb, Ta, Cr, Mo, W and Cl. See also Mugden and Young, J. Chem. Soc. P. 2988–2993, (1949).

Efforts have been made to epoxidize olefinic materials by reaction with hydrogen peroxide. See British Pat. No. 837,464 which purports to use various of Milas' catalysts, U.S. Pat. No. 2,786,854 which uses tungsten acid, U.S. Pat. No. 2,833,787 which uses an acid salt of Group VI metals such as tungsten and molybdenum, Belgian Pat. No. 860,776 which uses tungsten and molybdenum, U.S. Pat. No. 3,993,673 which uses an arsenic catalyst, U.S. Pat. No. 3,953,362 which uses a molybdenum catalyst, U.S. Pat. No. 4,026,908 which uses mercury plus molybdenum, tungsten vanadium, or titanium, U.S. Pat. No. 3,806,467 which uses tin plus molybdenum, tungsten, vanadium, selenium or boron, Bull. Chem. Soc. Jap. 42, P. 1604 (1969) uses selenium dioxide, U.S. Pat. No. 3,778,451 uses molybdenum, tungsten, vanadium, niobium, tantalum, uranium and rhenium, and the like. For various reasons these efforts have not been successful to the extent of commercialization.

Substantial work has been carried out involving the use of polymeric materials as reagents and as catalysts in organic syntheses. For a general discussion of this work reference can be made to an article by N. K. Mathur and R. E. Williams, J. Macromol. Sci.—Rev. Macromol Chem. C15 (1), 117–142 (1976). The preparation of solid selenium reagents is described by Michels et al. in Makromol. Chem., 2311–2320 (1976) as being prepared by supporting selenium compounds on aromatic polymer. Jacobson et al. JACS 101:23 p. 6946–6950, Nov. 7, 1979 describe arsonated polystyrenes and their use in the hydrogen peroxide epoxidation of olefins.

However, the present inventor is not aware of prior art showing the preparation of catalysts comprising tellurium chemically bound to a polymer containing aromatic groups or to the use of such catalysts in hydrogen peroxide epoxidations.

BRIEF SUMMARY OF THE INVENTION

The present invention relates to a novel solid catalyst comprised of tellurium chemically bound to solid organic polymer which contains aromatic groups, suitably a cross-linked polystyrene, as well as to the preparation of this novel catalyst.

The invention also relates to an improved epoxidation process wherein oxirane compounds are formed through reaction of olefinic compounds with hydrogen peroxide in the presence of the bound tellurium catalysts.

DETAILED DESCRIPTION OF THE INVENTION

In accordance with the present invention, a novel solid bound tellurium catalyst is provided which efficiently and selectively catalyzes the reaction between an olefinically unsaturated compound and hydrogen peroxide to produce the corresponding oxirane compound. Surprisingly, the epoxidations can be carried out in the presence of substantial amounts of water without excessive formation of glycols.

Tellurium compounds have been described in the art as epoxidation catalysts in the reaction between organic hydroperoxides and olefinic materials. See U.S. Pat. No. 3,351,635. However, the tellurium catalysts taught for the hydroperoxide reaction are not generally useful in a hydrogen peroxide epoxidation. The solid bound tellurium catalyst of this invention is thought to be unique in this respect.

A. THE CATALYST

The catalyst of this invention is a solid catalyst comprising tellurium chemically bound to an aromatic group-containing cross-linked polymer. Preferred polymers are co-polymers of styrene and divinyl benzene, the co-polymers cross linked to the extent of at least about 5% and preferably at least 20%. As used herein reference to the extent of cross linking refers to the weight percent of the cross linking agent based on total weight of polymer. A copolymer of styrene and divinyl benzene cross linked to the extent of 5% refers to a copolymer of 95% styrene and 5% divinyl benzene, by weight. Although the styrene-divinyl benzene polymers represent preferred polymers for use in the invention, cross-linked polymers containing aromatic groups generally can be employed. Examples of other such suitable polymers include polymers of alpha methyl styrene cross-linked with divinyl benzene and the like.

In a preferred method of catalyst preparation, a solution of a suitable tellurium compound is contacted with the solid polymer under conditions such that the tellurium compound reacts with polymer aromatic groups. For example, an especially desirable preparation procedure involves contacting tellurium tetrahalide, e.g., tellurium tetra-chloride, preferably in a halogenated solvent such as carbon tetrachloride, with the polymer under reactive conditions and for a time sufficient for the tellurium halide to react with polymer aromatic groups. The reaction can be schematically represented as follows:

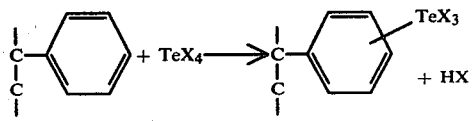

wherein X is a halide such as Cl.

The reaction is carried out over a broad range of temperatures, e.g., 20° C. to 250° C., with temperatures in the range 70° C. to 150° C. being preferred. Reaction time may vary although illustrative reaction times of 1 to 100 hours, preferably 24 to 72 hours are advantageous. A broad range of pressures can be employed consistent with maintaining the tellurium compound solution in the liquid phase. Illustrative pressures are 500 mmHg to 50 atm. although pressure is not critical. A generally preferred procedure is to carry out the reaction under reflux conditions with removal of solvent and hydrogen halide, separation of the hydrogen halide, and return to solvent liquid to the reaction zone.

The reacted polymer containing tellurium groups is then treated to convert it to the catalytically active form. The tellurium containing polymer is suitably hydrolyzed to convert the contained tellurium halide groups to tellurinic acid groups. Preferably the hydrolysis is accomplished by refluxing the tellurium halide containing polymer with aqueous base, e.g., aqueous sodium hydroxide or the like. In a particularly preferred embodiment the polymer which has been hydrolyzed with aqueous base is then treated with dilute aqueous acid, e.g., dilute HCl, and then thoroughly washed.

The reactive contact between the tellurium compound and the polymer is carried out until the resulting reaction product contains at least 1.2% by weight chemically bound tellurium expressed as elemental Te. Preferably the product contains 2 to 8% and most suitably 3 to 5% by weight chemically bound tellurium expressed as elemental Te.

Tellurium compounds used for reactions with the polymer are preferably tellurium halides such as tellurium tetrachloride but various other tellurium compounds can be used such as tellurides and ditellurides. The polymer may be halogenated to facilitate the reaction with certain tellurium compounds.

In addition to tellurium which is chemically bound to the aromatic polymers, generally catalysts prepared by the above procedure contain substantial amounts of non-bound tellurium deposited thereon. It has been found that the presence of non-bound tellurium causes significant non-selective decomposition of hydrogen peroxide and thus it is advantageous that the catalysts be treated or conditioned to remove non-bound tellurium.

One such treatment is simply to run the epoxidation reaction accepting the non-selective hydrogen peroxide decomposition during the initial stages until the non-bound tellurium is removed. However, a more advantageous method involves conditioning the catalyst by contacting it with aqueous or alcohol solutions of hydrogen peroxide for extended periods prior to beginning the epoxidation reaction. Illustratively, the catalyst is suspended in an aqueous or alcoholic solution of hydrogen peroxide at 20°-60° C. for 1 to 20 hours, filtered and washed with water until peroxide free before use.

B. EPOXIDATION

In accordance with the invention olefinically unsaturated compounds are reacted with hydrogen peroxide in the liquid phase in the presence of the novel bound tellurium catalysts to produce the corresponding oxirane compounds.

Both substituted and unsubstituted olefinic compounds can be epoxidized in accordance with the present invention. Illustrative olefinic compounds include ethylene, propylene, butene-1, butene-2, cyclohexene, octene-1, allyl alcohol, methyl oleate, soybean oil, allyl chloride, isoprene, isobutylene, styrene and the like.

A significant advantage of the invention is that the hydrogen peroxide reactant is preferably used in the form of the commercial grades of aqueous hydrogen peroxide solutions containing 30–70% by weight hydrogen peroxide. However, pure hydrogen peroxide, more dilute hydrogen peroxide, and the compounds liberating hydrogen peroxide at reaction conditions can also be employed.

It is generally advantageous in the epoxidation to employ a molar excess of the olefinic compound relative to hydrogen peroxide although this is not strictly necessary. Preferably 1.5 to 20 mols olefinic compound per mole hydrogen peroxide are used.

Reaction temperatures can vary over a broad range, e.g., from about 0° C. to 150° C. with temperatures of 40° C. to 80° C. being preferred. Temperatures at which excessive hydrogen peroxide decomposition takes place should be avoided. Pressure is not critical. Reaction pressures sufficient to maintain the liquid phase are employed. Illustrative pressures are 1 to 50 atms.

It is preferred to employ organic solvents in carrying out the epoxidation reaction. Solvents which do not attack the bound tellurium catalyst are used with both polar and non-polar solvents being useful. Polar solvents are preferred since these enhance the reaction rate. Illustrative solvents include the following: dioxane, methanol, t-butanol, acetone, ethers such as diethyl ether, furane, esters such as ethyl acetate, the carbitols, cellusolves, and the like. Solvents which are miscible with hydrogen peroxide are preferred. The presence of excessive amounts of water whereby product oxirane is hydrolyzed should be avoided.

The reaction can be carried out by suspending the solid bound catalyst in the reaction mixture with proper agitation during the epoxidation. Preferably, however, the olefinic material, hydrogen peroxide and solvent are passed through a bed of the solid catalyst particles in accordance with known procedures. Reaction times are regulated to provide the desired conversions; generally it is preferred to carry out the reaction to provide for substantially complete hydrogen peroxide conversion.

Product separations and recoveries are accomplished in accordance with well-known procedures.

The following examples illustrate the invention:

EXAMPLES

A. Catalyst Preparation

Solid tellurium catalysts were prepared from spherical macroreticular styrene-divinylbenzene copolymers manufactured by Rohm & Haas and designated as XAD-4 and XAD-2. The following table gives the characteristics of the starting copolymers.

TABLE I

Amberlite*, Spherical Macroreticular Styrene-Divinylbenzene Copolymer "Nontonic Polymeric Adsorbent"

|  | XAD-4 | XAD-2 |
|---|---|---|
| mesh size (wet) | 20–50 | 20–50 |
| true density g/ml | 1.02 | 1.03 |
| pore diameter A | 50 | 90 |
| surface area m$^2$/gm | 750 | 330 |
| porosity vol. % | 51 | 42 |
| max. op temp. C |  | 200 |
| uses |  | phenol removal |
| other names |  | Biobeads SM2 |
| bed vol. ml/g in benzene |  | 2.9 |
| mol. wt. exclusion limit |  | 14,000 |
| cross linking | " > 20% | "20%" |

*Trademark of Rohm and Haas

In each of runs 1–7, 20 grams of tellurium tetrachloride were admixed with 20 grams of dried XAD-4 or XAD-2 resin and with 200 grams of 1,1,2,2-tetrachloroethane and the resulting mixture was refluxed for 48 hours at reflux temperature (about 142° C.). Vapors were passed to a reflux condenser where tetrachloroethane was condensed and separated from hdyrogen chloride which is a product of the reaction. The condensed tetrachloroethane was dried and returned to the reaction. The reaction mixture was then cooled and suction filtered through a coarse fritted glass vacuum funnel. The dark colored solid tellurium containing catalyst beads were then washed with 100 ml portions of distilled acetone and vacuum filtered until the filtrate was clear. The washed catalyst beads were then placed in a petrie dish and dried at 110° C. overnight in a vacuum oven with a slight air purge.

The dried catalyst beads were then refluxed with 250 ml of 1N NaOH for 1 hour. The beads were suction filtered and washed with distilled water until the final washings had a pH of 7.0. The resin was then agitated in 100 ml of 6N HCl for 1 hour and after suction filtration the catalyst beads were washed with distilled water until the final wash had a pH of about 3.5. The catalyst beads which were brown in color were placed in a petrie dish and dried in a vacuum over at 110° C. under a slight air bleed until the catalyst beads came to a constant weight.

Catalysts prepared by this procedure from XAD-4 resin typically contained 6–9 weight percent tellurium expressed as elemental tellurium while those from XAD-2 had higher tellurium content and were used in Runs 1–7 to catalyze olefinic compound epoxidations without further treatment.

The catalyst used in Runs 8 and 9 were prepared by admixing about 20 grams of tellurium tetrachloride, 20 grams of the cross linked XAD-2 styrene-divinyl benzene copolymer, and 200 ml of 1,1,2,2-tetrachloroethane, heated to reflux temperatures (about 142° C.) and refluxed for about 48 hours. Vapors were passed to a reflux condenser where tetrachloroethane was condensed and separated from hydrogen chloride which is a product of the reaction. The condensed tetrachloroethane was dried and returned to the reaction.

Each reaction mixture, after 48 hours refluxing, was cooled and the solid polymer containing bound tellurium was filtered and washed with successive 200 ml portions of carbon tetrachloride and ethyl ether. The washed solid was dried and then refluxed for one hour with 400 ml of 1N sodium hydroxide.

After cooling to room temperature, the condenser was washed down with 100 ml of distilled water and 100 ml of concentrated hydrochloric acid was slowly added. The pH, as determined by pH paper was 1. The solid polymer containing bound tellurium was then filtered and washed with sufficient distilled water to remove all traces of HCl. The catalyst was dried at 50° C. in a vacuum oven for about 48 hours.

B. Epoxidations

Catalysts prepared by the above procedures were used to catalyze the epoxidation of olefinic materials with hydrogen peroxide by the following general procedure:

A solution of olefinic material, aqueous hydrogen peroxide (30% or 90% by weight $H_2O_2$) and solvent was prepared and catalyst added thereto. The resulting mixture was heated to 60° C. and reacted with constant agitation. Pressure was substantially atmospheric. Samples were taken and analyzed for peroxide and epoxide. The hydrogen peroxide was determined by standard ceric sulfate titration, while the epoxides were determined either by gas chromatography or titration. The following table shows the results obtained:

TABLE

| | Wt. % $H_2O_2$ in water | g $H_2O_2$ soln | Olefin | g. Olefin | Molar ratio Olefin/$H_2O_2$ | Solvent | g Solvent | Resin | Wt. % Te | g Catalyst | Temp °C. | Time Hrs. | Wt. % Epoxide | Wt. % $H_2O_2$ | % $H_2O_2$ Conv. | % Sel. to Epoxide based on $H_2O_2$ |
|---|---|---|---|---|---|---|---|---|---|---|---|---|---|---|---|---|
| 1 | 90 | 0.91 | Cyclohexene | 5.9 | 3.0 | Acetonitrile | 33.2 | XAD-2 | 11.4 | 2.0 | 60.0 | 6.0 | 2.8 | 0.3 | 86.5 | 52.7 |
| 2 | 90 | 0.91 | Cyclohexene | 5.9 | 3.0 | Acetonitrile | 33.2 | XAD-4 | 6.7 | 0.5 | 60.0 | 6.0 | 5.4 | 0.1 | 94.9 | 94.5 |
| 3 | 90 | 0.91 | Cyclohexene | 5.9 | 3.0 | Absolute Ethanol | 33.2 | XAD-4 | 6.7 | 0.5 | 60.0 | 6.0 | 5.6 | 0.06 | 97.2 | 95.6 |
| 4 | 90 | 0.92 | Cyclohexene | 5.9 | 3.0 | Dioxane | 33.2 | XAD-4 | 6.7 | 0.5 | 60.0 | 6.0 | 3.6 | 0.7 | 66.1 | 87.2 |
| 5 | 90 | 1.81 | Methyloleate | 2.5 | 0.16 | Acetonitrile | 3.52 | XAD-4 | 6.7 | 2.0 | 60.0 | 6.0 | 6.5 | 2.83 | 30.4 | 54.6 |
| 6 | 90 | 1.80 | Hexadecene-1 | 5.3 | 0.5 | t-butylalcohol | 33.8 | XAD-4 | 9.1 | 1.0 | 60.0 | 6.0 | 4.2 | 1.0 | 51.7 | 56.0 |
| 7 | 90 | 1.81 | Tetradecene-7 | 4.7 | 0.5 | t-butylalcohol | 33.5 | XAD-4 | 7.8 | 2.0 | 60.0 | 6.0 | 7.3 | 2.1 | 48.8 | 56.0 |

TABLE-continued

| | Wt. % $H_2O_2$ in water | g $H_2O_2$ soln | Olefin | g. Olefin | Molar ratio Olefin/ $H_2O_2$ | Solvent | g Solvent | Resin | Wt. % Te | g Catalyst | Temp °C. | Time Hrs. | Wt. % Epoxide | Wt. % $H_2O_2$ | % $H_2O_2$ Conv. | % Sel. to Epoxide based on $H_2O_2$ |
|---|---|---|---|---|---|---|---|---|---|---|---|---|---|---|---|---|
| 8 | 30 | 2.1 | Trans-octene-2 | 1.1 | 1.9 | Dioxane | 17.0 | XAD-2 | 4.5 | 1.0 | 60.0 | 24.0 | 1.0 | 2.8 | 11.1 | 73.0[A] |
| 9 | 30 | 2.1 | Cis-octene-2 | 1.1 | 1.9 | Dioxane | 17.0 | XAD-2 | 4.5 | 1.0 | 60.0 | 24.0 | 0.96 | 2.9 | 8.4 | 89.8[B] |

[A]Only trans-octene-2,3-oxide was formed
[B]Only Cis-octene-2,3-oxide was formed

I claim:

1. The method of preparing an oxirane compound which comprises reacting an olefinically unsaturated compound with hydrogen peroxide in the presence of a solid catalyst comprising tellurium chemically bound to a cross linked polymer which contains aromatic groups.

2. The method of claim 1 wherein the catalyst comprises 0.2 to 20% by weight tellurium expressed as elemental tellurium chemically bound to an aromatic group.

* * * * *

UNITED STATES PATENT AND TRADEMARK OFFICE
CERTIFICATE OF CORRECTION

PATENT NO.   :   4,480,113
DATED        :   October 30, 1984
INVENTOR(S)  :   William F. Brill It is certified that error appears in the above-identified patent and that said Letters Patent is hereby corrected as shown below:

Column 8, line 15 - after "bound to" insert -- an aromatic group of --

Column 8, line 20 - after "group" and before the (.) insert -- of a cross linked polymer which contains aromatic groups --

Signed and Sealed this

Twenty-eighth Day of May 1985

[SEAL]

Attest:

DONALD J. QUIGG

Attesting Officer    Acting Commissioner of Patents and Trademarks